United States Patent [19]

DiNinno et al.

[11] Patent Number: 4,978,659
[45] Date of Patent: Dec. 18, 1990

[54] 2-(HETEROARYLIUMALKYL)PHENYL CARBAPENEM ANTIBACTERIAL AGENTS

[75] Inventors: Frank P. DiNinno, Old Bridge; David A. Muthard, Freehold; Thomas N. Salzmann, North Plainfield, all of N.J.

[73] Assignee: Merck & Co., Inc., Rahway, N.J.

[21] Appl. No.: 396,165

[22] Filed: Aug. 21, 1989

Related U.S. Application Data

[63] Continuation-in-part of Ser. No. 9,865, Feb. 2, 1987, abandoned.

[51] Int. Cl.$^5$ .................. C07D 487/04; A61K 31/40
[52] U.S. Cl. ..................................... 514/210; 540/302
[58] Field of Search ......................... 540/302; 514/210

[56] References Cited

U.S. PATENT DOCUMENTS 4,729,993 3/1988 Christenson ..................... 514/210

Primary Examiner—Robert Gerstl
Attorney, Agent, or Firm—Raymond M. Speer; Hesna J. Pfeiffer

[57] ABSTRACT

Carbapenems having the formula:

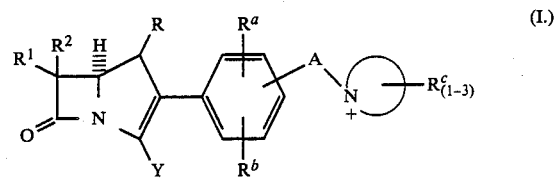

are useful antibacterial agents.

14 Claims, No Drawings

2-(HETEROARYLIUMALKYL)PHENYL CARBAPENEM ANTIBACTERIAL AGENTS

REFERENCE TO RELATED APPLICATIONS

This is a continuation-in-part of application Ser. No. 009,865, filed Feb. 2, 1987, abandoned.

BACKGROUND OF THE INVENTION

The present invention relates to antibacterial agents of the carbapenem class, in which the 2-position sidechain is characterized by a phenyl moiety, optionally substituted, to which is attached, usually through an alkyl bridge, a nitrogen-containing heterocycle, with attachment being through the nitrogen atom, as described in more detail further below.

Thienamycin was an early carbapenem antibacterial agent having a broad spectrum; it has the following formula:

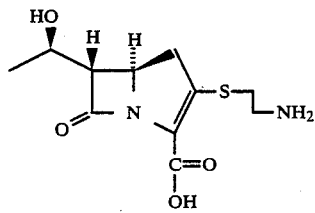

Later, N-formimidoyl thienamycin was discovered; it has the formula:

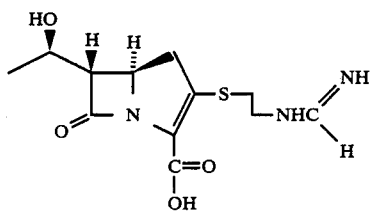

The 2-(heteroaryliumalkyl)phenyl carbapenems of the present invention have an antibacterial spectrum and potency equal to or greater than, in most cases, that of either thienamycin or N-formimidoyl thienamycin. The compounds of the present invention are also more resistant than thienamycin or N-formimidoyl thienamycin to degradation by the dehydropeptidase enzyme DHP-I, thus permitting greater therapeutic application of the compounds.

More recently, carbapenem antibacterial agents have been described which have a 2-substituent which is an aryl moiety optionally substituted by, e.g., aminomethyl and substituted aminomethyl. These agents are described in U.S. Pat. Nos. 4,543,257 and 4,260,627 and have the formula:

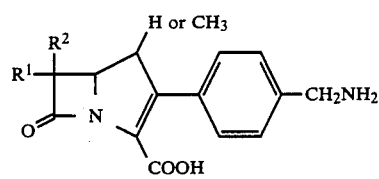

However, these compounds belong to a different class from those of the present invention and are distinguished by different physiological properties.

SUMMARY OF THE INVENTION

The present invention provides novel carbapenem compounds of the formula:

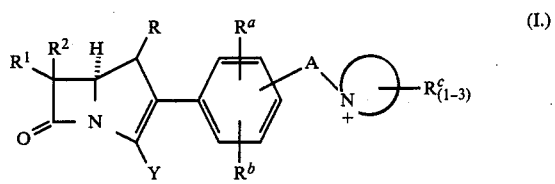

wherein:

R is H or $CH_3$;

$R^1$ and $R^2$ are independently; H, $CH_3-$, $CH_3CH_2-$, $(CH_3)_2CH-$, $HOCH_2-$, $CH_3CH(OH)-$, $(CH_3)_2C(OH)-$, $FCH_2CH(OH)-$, $F_2CHCH(OH)-$, $F_3CCH(OH)-$, $CH_3CH(F)-$, $CH_3CF_2-$, or $(CH_3)_2C(F)-$;

$R^a$, $R^b$ and $R^c$ [$R^c$ represents from 1 to 3 substituents which may be the same or different and is (are) on the carbon ring atom(s) or nitrogen heteroatom(s), if such is (are) present] are independently selected from the group consisting of:

(a) a trifluoromethyl group: $-CF_3$;

(b) a halogen atom: $-Br$, $-Cl$, $-F$, or $-I$;

(c) $C_1-C_4$ alkoxy radical: $-OC_{1-4}$ alkyl;

(d) a hydroxy group: $-OH$;

(e) ($C_1-C_6$ alkyl) carbonyloxy radical:

alkyl;

(f) a carbamoyloxy radical which is unsubstituted or substituted on nitrogen with one or two $C_1-C_4$ alkyl groups:

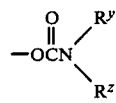

where $R^y$ and $R^z$ are independently H or $C_{1-4}$ alkyl;

(g) a $C_1-C_6$ alkylthio radical, $C_1-C_6$ alkylsulfinyl radical or $C_1-C_6$ alkylsulfonyl radical:

alkyl where n=0-2, and the alkyl portion is optionally substituted by cyano;

(h) a sulfamoyl group which is unsubstituted or substituted on nitrogen by one or two $C_1-C_4$ alkyl groups:

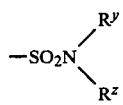

where $R^y$ and $R^z$ are as defined above;
(i) an amino group, or a mono ($C_1$–$C_4$ alkyl) amino or di($C_1$–$C_4$ alkyl) amino group:

where $R^y$ and $R^z$ are defined above;
(j) a formylamino group:

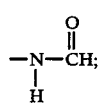

(k) ($C_1$–$C_6$ alkyl)carbonylamino radical:

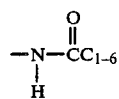

alkyl;
(l) a ($C_1$–$C_4$ alkoxy) carbonylamino radical:

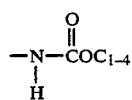

alkyl;
(m) a ureido group in which the terminal nitrogen is unsubstituted or substituted with one or two $C_1$–$C_4$ alkyl groups:

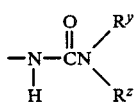

where $R^y$ and $R^z$ are as defined above;
(n) a sulfonamido group:

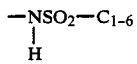

alkyl;
(o) a cyano group: —CN;
(p) a formyl or acetalized formyl radical:

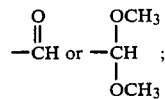

(q) ($C_1$–$C_6$ alkyl)carbonyl radical wherein the carbonyl is free or acetalized:

alkyl or

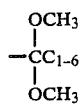

alkyl;
(r) phenylcarbonyl;
(s) a hydroximinomethyl radical in which the oxygen or carbon atom is optionally substituted by a $C_1$–$C_4$ alkyl group:

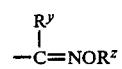

where $R^y$ and $R^z$ are as defined above;
(t) a ($C_1$–$C_6$ alkoxy)carbonyl radical:

alkyl;
(u) a carbamoyl radical which is unsubstituted or substituted on nitrogen by one or two $C_1$–$C_4$ alkyl groups:

where $R^y$ and $R^z$ are as defined above;
(v) an N-hydroxycarbamoyl or N($C_1$–$C_4$ alkoxy)-carbamoyl radical in which the nitrogen atom may be additionally substituted by a $C_1$–$C_4$ alkyl group:

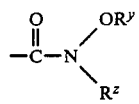

where $R^y$ and $R^z$ are as defined above;
(w) a thiocarbamoyl group:

(x) an amidino group

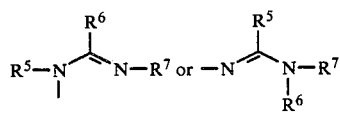

where $R^5$, $R^6$ and $R^7$ are independently hydrogen, $C_1$–$C_4$alkyl or wherein two of the alkyl groups together form a $C_2$–$C_6$alkylidene radical optionally interrupted by a heteroatom and joined together to form a ring;
(y) a carboxamidino group

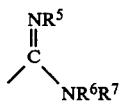

where $R^5$, $R^6$ and $R^7$ are as defined above;
(z) a guanidinyl group where $R^6$ in (y) above is $NR^8R^9$ and $R^8$ and $R^9$ are as defined for $R^5$ through $R^7$ above;
(aa) hydrogen;
(ab) $C_2$-$C_6$ alkenyl radical;
(ac) $C_2$-$C_6$ alkynyl radical;
(ad) $C_3$-$C_7$ cycloalkyl radical;
(ae) $C_3$-$C_7$ cycloalkyl methyl radical;
(af) $C_5$-$C_7$ cycloalkenyl radical;
(ag) phenyl, except that only $R^c$ may be phenyl;
(ah) $C_1$-$C_6$ alkyl radical;
(ai) $C_1$-$C_4$ alkyl monosubstituted by one of the substituents (a)-(ag) above;
(aj) an anionic function selected from the group consisting of: phosphono [P=O(OM$^c$)$_2$]; alkylphosphono {P=O(OM$^c$)—[O(C$_1$-C$_4$ alkyl)]}; alkylphosphinyl [P=O(OM$^c$)—(C$_1$-C$_4$alkyl)]; phosphoramido [P=O(OMc)N(R$^y$)R$^z$ and P=O(OM$^c$)NHR$^x$]; sulfino (SO$_2$M$^c$); sulfo (SO$_3$M$^c$); acylsulfonamides selected from the structures CONM$^c$SO$_2$R$^x$, CONM$^c$SO$_2$N(R$^y$)R$^z$, SO$_2$NM$^c$CON(R$^y$)R$^z$; and SO$_2$NM$^c$CN, where
$R^x$ is phenyl or heteroaryl, where heteroaryl is as defined below except that there is no quaternary nitrogen and attachment through nitrogen is optional; and the phenyl and heteroaryl are optionally mono-substituted by R$^q$; M$^c$ is hydrogen or an alkali metal; R$^y$ and R$^z$ are as defined above; where R$^q$ is a member selected from the group consisting of —OH; —OCH$_3$—; —CN; —C(O)NH$_2$; —OC-(O)NH$_2$; —OC(O)N(CH$_3$)$_2$; —SO$_2$NH$_2$; —SO$_2$N(CH$_3$)$_2$; —SOCH$_3$; —F; —CF$_3$; tetrazolyl; and —COOM$^a$, where M$^a$ is hydrogen, alkali metal, methyl or phenyl;
A is para (p) or meta (m) with respect to the point of attachment of the phenyl ring to the carbapenem nucleus, and is (CH$_2$)$_m$—Q—(CH$_2$)$_n$, where m is 0 to 2 and n is 1 or 2; and Q is a covalent bond; O; S; SO; SO$_2$; NH; or N(C$_1$-C$_4$ alkyl);

is a monocyclic aromatic hydrocarbon group having 5 or 6 ring atoms in which one of the carbon atoms has been replaced by a nitrogen atom and attachment of said group is by way of said nitrogen atom; and said nitrogen atom is, furthermore, quaternary by virtue of the attachment bond and the ring bonds; and in which one additional carbon atom is optionally replaced by a heteroatom selected from O and S, or from 1 to 3 additional carbon atoms are each optionally replaced by a nitrogen heteroatom; and
Y is selected from:

(i) COOH or a pharmaceutically acceptable ester thereof;
(ii) COOM wherein M is an alkali metal or other pharmaceutically acceptable salt;
(iii) COOM wherein M is a negative charge in the case where a permanent positive charge exists elsewhere in the molecule.

The $R^c_{(1-3)}$ substituent represents from 1 to 3 substituents which may be the same or different and are selected on an independent basis. A single such substituent is preferred.

The overall molecule must be electronically balanced. Since a quaternary nitrogen is always present in the compounds of the present invention, a balancing anion must also be present. This is usually accomplished by having Y be COO$^-$. However, where Y is, e.g., a pharmaceutically acceptable ester, a counterion (anion) Z$^-$ must be provided, or alternatively, an anionic substituent might be utilized. Further, it is within the scope of this invention to utilize an anionic substituent where the quaternary nitrogen is already balanced by Y=COO$^-$. In that case, it will be understood that it is necessary to provide a counterion (cation) for the anionic substituent. However, it is well within the skill of a medicinal chemist, to whom there is available many suitable anionic and cationic counterions, to make such choices.

With reference to the above definitions, "alkyl" means a straight or branched chain aliphatic hydrocarbon radical.

The term "heteroatom" means N, S, or O, selected on an independent basis.

Under the definition of "Y", the term "pharmaceutically acceptable ester or salt" refers to those salt and ester forms of the compounds of the present invention which would be apparent to the pharmaceutical chemist, i.e., those which are non-toxic and which would favorably affect the pharmacokinetic properties of said compounds, their palatability, absorption, distribution, metabolism and excretion. Other factors, more practical in nature, which are also important in the selection, are cost of raw materials, ease of crystallization, yield, stability, hygroscopicity, and flowability of the resulting bulk drug. Since the compounds of the present invention may be carboxylates, the salts would be cations such as benzathine, chloroprocaine, choline, diethanolamine, meglumine and procaine. The metallic cations such as aluminum, calcium, lithium, magnesium and zinc are potential choices. The alkali metal cations sodium and potassium are specifically defined. It will also be noted that the compounds of the present invention are potentially internal salts or zwitterions, since under physiological conditions the carboxyl group may be anionic, and this electronic charge will be balanced off internally against the cationic charge of the heteroarylium group. Where this is not the case, it is recognized that a counterion must be present. This counterion is selected from the group of suitable pharmaceutical anions, e.g., chloride, phosphate and tartrate.

It is preferred that when one of $R^1$ or $R^2$ is H, the other is (R)—CH$_3$CH(OH)— or (R)—CH$_3$CH(F)—, and (R)—CH$_3$CH(OH)— is most preferred. Further, it is preferred that the configuration at C-6 is (S), and that at C-5 is (R).

Representative A groups are —CH$_2$—, —CH$_2$CH$_2$—, and —OCH$_2$CH$_2$—. Preferred is —CH$_2$—.

Representative $R^c$ groups are —CH$_3$, —CH$_2$CH$_3$, —(CH$_2$)$_3$CH$_3$, —OCH$_3$, —SCH$_3$,

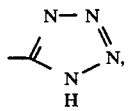

—COOH, —NHCH$_2$COOH, —OH, —CH$_2$OH, —CH$_2$COOH, —CH$_2$CH$_2$COOH, —CH$_2$CONH$_2$, —CH$_2$CH$_2$S+(CH$_3$)$_2$, —CH$_2$CH$_2$SO$_3$H,

—CONH$_2$, —SO$_2$NH$_2$, —SO$_3$H, —NH$_2$, —N(CH$_3$)$_2$, —CON(CH$_3$)$_2$, —NHCH$_3$, —CH$_2$NH$_2$, —CN, —CH$_2$CN, —CH$_2$SCH$_3$, —CH$_2$SO$_3$−, —CH$_2$SOCH$_3$, —CH$_2$SO$_2$CH$_3$, —SO$_2$CH$_3$, —SOCH$_3$, —CH$_2$OCH$_3$,

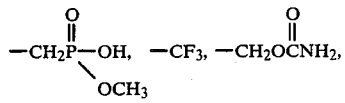

—CH$_2$SO$_2$NH$_2$, —SCH$_2$CH$_2$CN, Br, Cl, F, —SCF$_3$, —CH$_2$SCF$_3$, and —SCH$_2$CF$_3$.

Useful examples of the

moiety are the following:

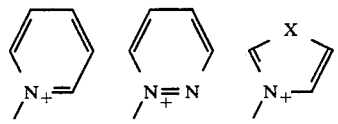

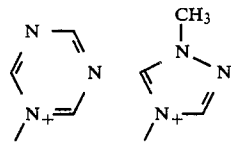

where X=O, S or NR$^e$, where R$^e$=C$_1$-C$_4$alkyl, or CH$_2$COR$^f$, where R$^f$=OCH$_3$, OCH$_2$-(phenyl), NH$_2$, CH$_2$SO$_3$−M+, where M+=Na+ or K+.

The pyridinium group is preferred since it provides the desired properties of good antibacterial spectrum and potency combined with chemical stability and satisfactory resistance to hydrolysis by the dihydropeptidase (DHP-I) enzyme, together with ready availability and ease of handling as a starting material. However, any of the other groups set out above, as well as those falling within the definition of

set out herein but not specifically described above, are also suitable, although perhaps in some cases less desirable in terms of one or more of the criteria mentioned above.

While R=H is usually preferred, there are instances in which R=CH$_3$ may provide improved chemical stability, water solubility, or pharmacokinetic behavior. The substituent R=CH$_3$ may be of either configuration, i.e., the α or β-stereoisomer.

For most of the compounds exemplified herein, the R substituent is hydrogen. This is the result not only of a more facile synthesis for such compounds, but also of a preference for R=hydrogen based on the superior antibacterial activity of such compounds.

With regard to all of the preferred substituents described above, the following compounds are preferred embodiments of the present invention:

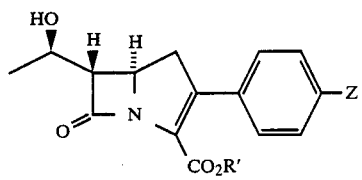

where Z is selected from:

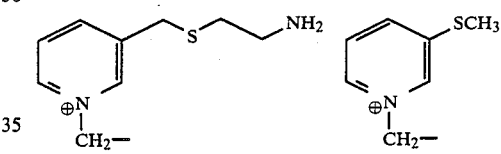

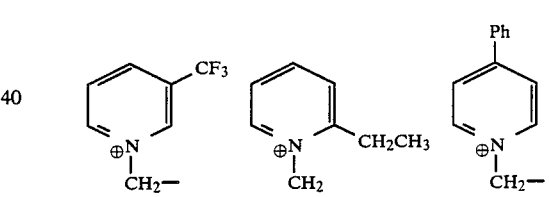

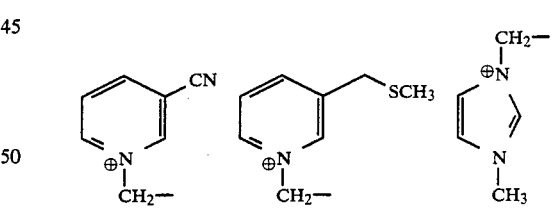

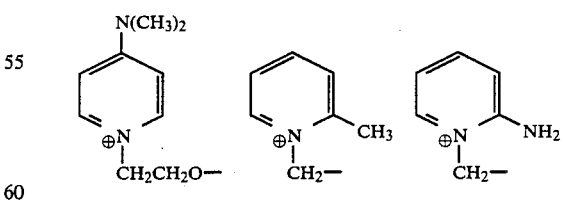

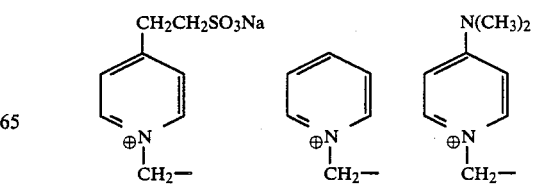

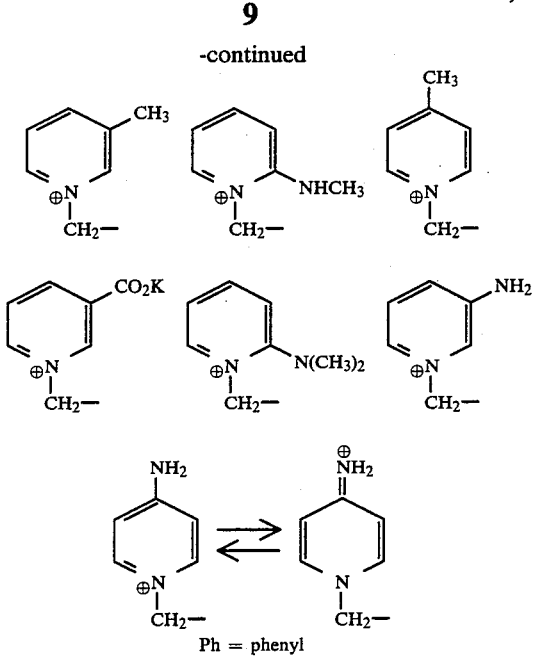

Ph = phenyl where R' is a negative charge or a pharmaceutically acceptable ester.

Compounds of the present invention may be tautomeric, as is evident from the structure depicted in formula (10) above. Both isomeric forms of such a tautomeric compound are intended to be included within the scope of the present invention and therefore are contemplated to be within the structure of Formula (I).

The carbapenem compounds of the present invention are useful per se and in their pharmaceutically acceptable salt and ester forms in the treatment of bacterial infections in animal and human subjects. Conveniently, pharmaceutical compositions may be prepared from the active ingredients in combination with pharmaceutically acceptable carriers. Thus, the present invention is also concerned with pharmaceutical compositions and methods of treating bacterial infections utilizing as an active ingredient the novel carbapenem compounds of the present invention.

The pharmaceutically acceptable salts referred to above include non-toxic acid addition salts. In those cases where the Formula I compounds possess a basic functional group, they can be used in the form of salts derived from inorganic or organic acids. Included among such salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others. Water or oil-soluble or dispersible products are thereby obtained.

The pharmaceutically acceptable esters of the novel carbapenem compounds of the present invention are such as would be readily apparent to a medicinal chemist, and include, for example, those described in detail in U.S. Pat. No. 4,309,438, Column 9, line 61 to Column 12, line 51, which is incorporated herein by reference. Included within such pharmaceutically acceptable esters are those which are hydrolyzed under physiological conditions, such as pivaloyloxymethyl, acetoxymethyl, phthalidyl, indanyl and methoxymethyl, and those described in detail in U.S. Pat. No. 4,479,947, which is incorporated herein by reference.

The compounds of the present invention are valuable antibacterial agents active against various Gram-positive and Gram-negative bacteria and accordingly find utility in human and veterinary medicine. Representative pathogens which are sensitive to the antibacterial agents of the present invention include various species or strains of the following: Staphylococcus, Enterococcus, Escherichia coli, Klebsiella, Enterobacter, Bacillus, Salmonella, Pseudomonas, Serratia and Proteus. The antibacterials of the invention are not limited to utility as medicaments; they may be used in all manner of industry, for example: additives to animal feed, preservation of food, disinfectants, and in other industrial systems where control of bacterial growth is desired. For example, they may be employed in aqueous compositions in concentrations ranging from 0.1 to 100 parts of antibiotic per million parts of solution in order to destroy or inhibit the growth of harmful bacteria on medical and dental equipment and as bactericides in industrial applications, for example in waterbased paints and in the white water of paper mills to inhibit the growth of harmful bacteria.

The compounds of this invention may be used in any of a variety of pharmaceutical preparations. They may be employed in capsule, powder form, in liquid solution, or in suspension. They may be administered by a variety of means; those of principal interest include: topically or parenterally by injection (intravenously or intramuscularly).

Compositions for injection, a preferred route of delivery, may be prepared in unit dosage form in ampules, or in multidose containers. The compositions may take such forms as suspensions, solutions, or emulsions in oily or aqueous vehicles, and may contain formulatory agents. Alternatively, the active ingredient may be in powder form for reconstitution, at the time of delivery, with a suitable vehicle, such as sterile water. Topical applications may be formulated in hydrophobic or hydrophilic bases as ointments, creams, lotions, paints, or powders.

The dosage to be administered depends to a large extent upon the condition and size of the subject being treated as well as the route and frequency of administration—the parenteral route by injection being preferred for generalized infections. Such matters, however, are left to the routine discretion of the therapist according to principles of treatment well known in the antibacterial art. In general, a daily dosage consists of from about 5 to about 600 mg of active ingredient per kg of body weight of the subject in one or more treatments per day. A preferred daily dosage for adult humans lies in the range of from about 10 to 240 mg of active ingredient per kg of body weight. Another factor influencing the precise dosage regimen, apart from the nature of the infection and peculiar identity of the individual being treated, is the molecular weight of the chosen species of this invention.

The compositions for human delivery per unit dosage, whether liquid or solid, may contain from 0.1% to 99% of active material, the preferred range being from about 10–60%. The composition will generally contain from about 15 mg to about 1500 mg of the active ingredient; however, in general, it is preferable to employ a dosage amount in the range of from about 250 mg to 1000 mg. In parenteral administration, the unit dosage is usually the pure compound I in sterile water solution or in the form of a soluble powder intended for solution.

The preferred method of administration of the Formula I antibacterial compounds is parenteral by i.v. infusion, i.v. bolus, or i.m. injection.

For adults, 5–50 mg of Formula I antibacterial compounds per kg of body weight given 2, 3, or 4 times per day is preferred. Preferred dosage is 250 mg to 1000 mg of the Formula I antibacterial given two (b.i.d.) three (t.i.d.) or four (q.i.d.) times per day. More specifically, for mild infections, and particularly urinary tract infections, a dose of 250 mg t.i.d. or q.i.d. is recommended. For moderate infections against highly susceptible gram positive and gram negative organisms, a dose of 500 mg t.i.d. or q.i.d. is recommended. For severe, life-threatening infections against organisms at the upper limits of sensitivity to the antibiotic, a dose of 1000 mg t.i.d. or q.i.d. is recommended.

For children, a dose of 5–25 mg/kg of body weight given 2, 3, or 4 times per day is preferred; a dose of 10 mg/kg t.i.d. or q.i.d. is usually recommended.

Antibacterial compounds of Formula I are of the broad class known as carbapenems or 1-carbadethiapenems. Naturally occurring carbapenems are susceptible to attack by a renal enzyme known as dehydropeptidase (DHP). This attack or degradation may reduce the efficacy of the carbapenem antibacterial agent. The compounds of the present invention, on the other hand, are significantly less subject to such attack, and therefore may not require use of a DHP inhibitor. However, such use is optional and contemplated to be a part of the present invention. Inhibitors of DHP and their use with carbapenem antibacterial agents are disclosed in the prior art [see European patent applications No. 79102616.4 filed July 24, 1979 (Pat. No. 0 010 573); 79102615.6, filed July 24, 1979 (Pat. No. 0 007 614); and No. 82107174.3, filed Aug. 9, 1982 (Publication No. 0 072 014)].

The compounds of the present invention may, where DHP inhibition is desired or necessary, be combined or used with the appropriate DHP inhibitor as described in the aforesaid patents and published application. Thus, to the extent that the cited European patent applications (1) define the procedure for determining DHP susceptibility of the present carbapenems and (2) disclose suitable inhibitors, combination compositions and methods of treatment, they are incorporated herein by reference. A preferred weight ratio of Formula I compound:DHP inhibitor in the combination compositions is about 1:1. A preferred DHP inhibitor is 7-(L-2-amino-2-carboxyethylthio)-2-(2,2-dimethylcyclopropanecarboxamide)-2-heptenoic acid or a useful salt thereof.

These combination compositions and their use are further embodiments of the present invention.

DETAILED DESCRIPTION OF THE INVENTION

The 2-(heteroaryliumalkyl)phenyl carbapenem compounds of the present invention may be prepared in accordance with well known procedures in the art. Particularly useful are the following synthetic schemes in which the symbols R, $R^1$, $R^2$, $R^a$, $R^b$, $R^c$, A and

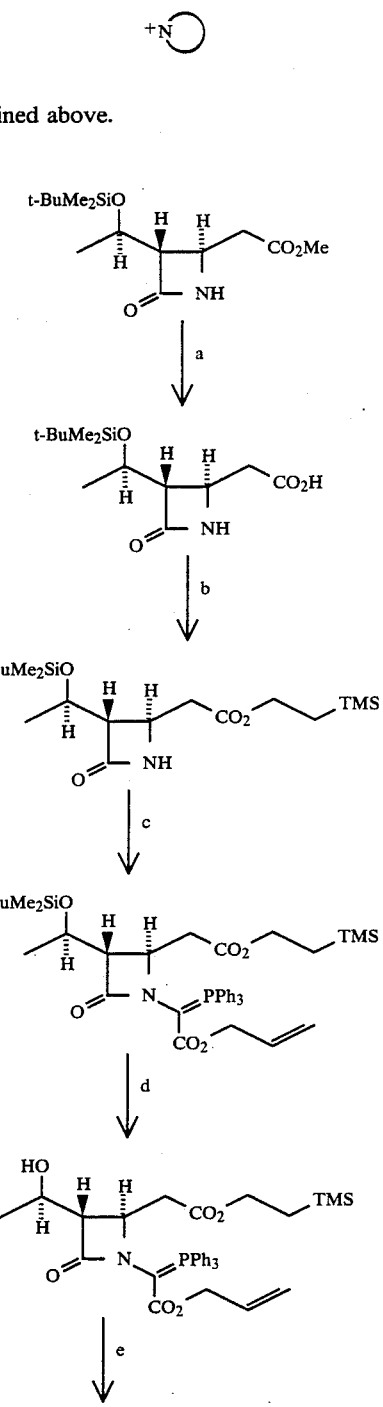

are as defined above.

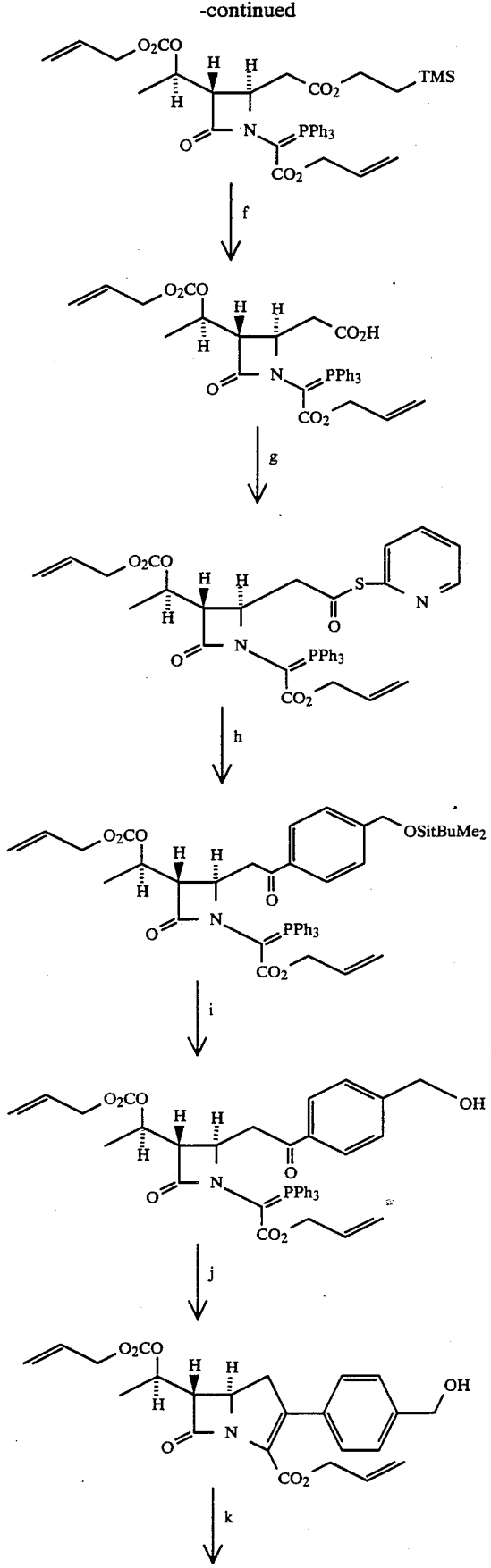

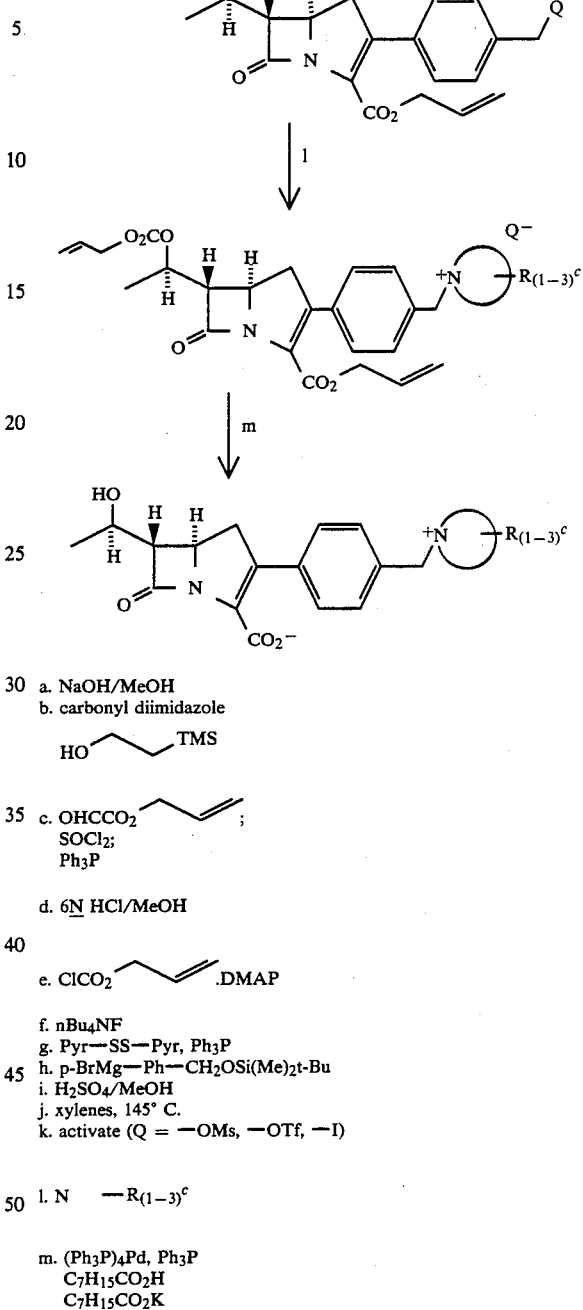

a. NaOH/MeOH
b. carbonyl diimidazole

HO⁀TMS c. OHCCO₂⁀ ;
SOCl₂;
Ph₃P d. 6N HCl/MeOH e. ClCO₂⁀.DMAP f. nBu₄NF
g. Pyr—SS—Pyr, Ph₃P
h. p-BrMg—Ph—CH₂OSi(Me)₂t-Bu
i. H₂SO₄/MeOH
j. xylenes, 145° C.
k. activate (Q = —OMs, —OTf, —I)

l. N⏝—R$_{(1-3)}^c$ m. (Ph₃P)₄Pd, Ph₃P
C₇H₁₅CO₂H
C₇H₁₅CO₂K

The steps for preparing the 2-(p-hydroxymethylphenyl)carbapenem intermediate are well known in the art and are explained in ample detail in U.S. Pat. Nos. 4,260,627 and 4,543,257, which are incorporated herein by reference. Addition of the heteroaryliumalkyl moiety is as represented in the schematic diagram above.

The bridging element "A" is already in place when the phenyl group becomes a part of the carbapenem compound at the time of cyclization. In the preferred embodiments of the present invention, the bridging element "A" is simply alkyl. However, it is also an embodiment of the present invention to include a heteroatom in the alkyl chain, as defined further above.

Preparation of such a heteroatom-containing alkyl bridge is in accordance with the following synthetic scheme:

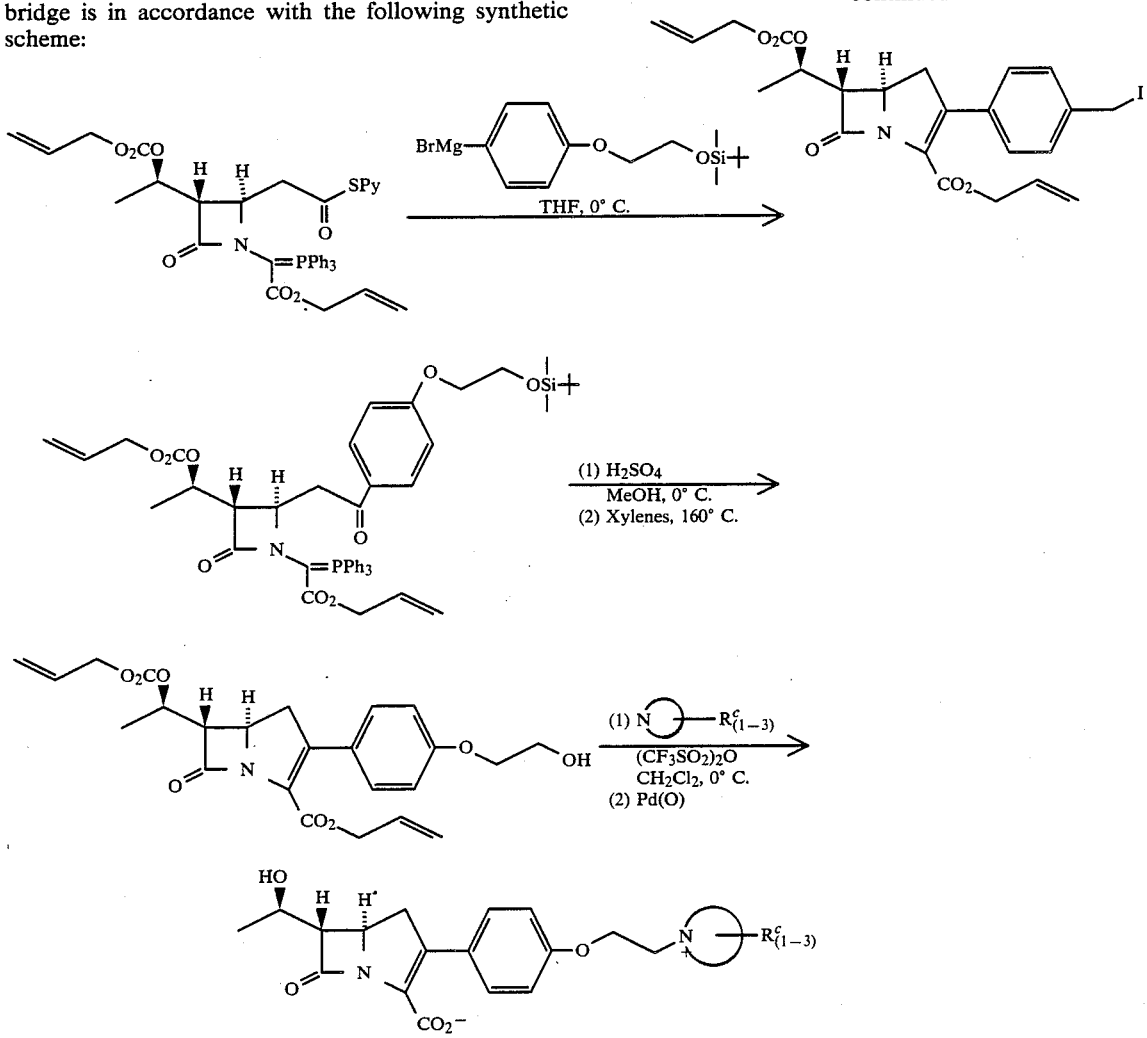

The bridging element terminates in a hydroxyl group which is then changed to an active leaving group, e.g., iodide. Treatment with the desired heteroaryl reactant directly provides the heteroaryliumalkylphenyl side-chain. More particularly, three alternative procedures may be utilized for addition of the heteroarylium group.

ACTIVATION OF THE PHENYL—A—OH GROUP

This step may be carried out in accordance with well-known procedures, some of which are exemplified in the following equations.

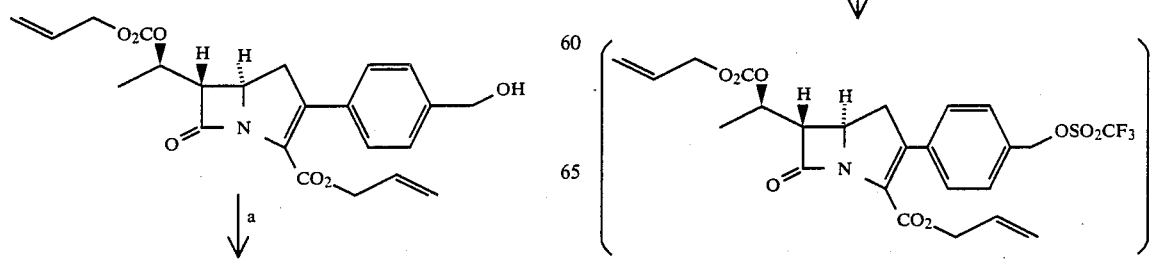

-continued

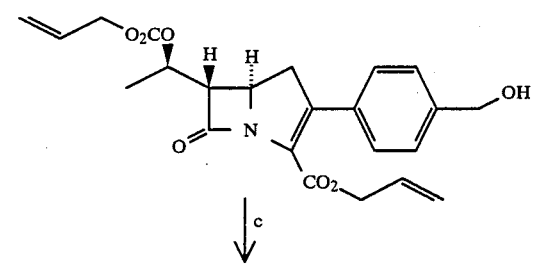

↓ c

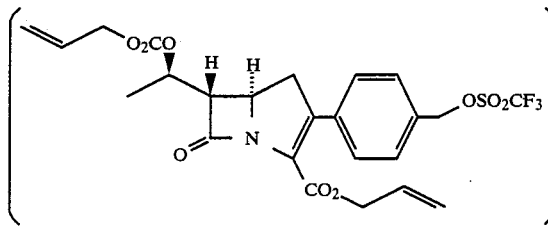

a (1) MsCl, (2) NaI; or (PhO)₃PMe⁺I⁻
b AgOSO₂CF₃
c (CF₃SO₂)₂O

In words relative to the equations, the hydroxyl group may be converted to a methanesulfonate group by treating with methanesulfonyl chloride in the presence of triethylamine. A suitable solvent, e.g., dichloromethane, is employed and the reaction is carried out at reduced temperatures. In turn, the methanesulfonate intermediate may be converted to the more reactive iodide derivative by treatment with sodium iodide in a suitable solvent, e.g., acetone, at reduced or ambient temperatures. Alternatively, the hydroxyl group may be directly converted into the iodide group by common methods known in the art. For example, treatment of the hydroxyl group with methyl triphenoxyphosphonium iodide in a suitable solvent, such as dimethylformamide, at reduced or ambient temperatures, directly provides the desired iodide. Further, the hydroxyl group may be converted into the very reactive trifluoromethanesulfonate group. However, such an activating group cannot be isolated by conventional techniques but may be formed and used in situ. Thus, treatment of the hydroxyl group with trifluoromethanesulfonic acid anhydride in the presence of, usually, the reacting heteroaromatic base in a suitable solvent, such as dichloromethane, at reduced temperatures provides for the in situ generation of this activating group. Alternatively, the trifluoromethanesulfonate group may be generated in situ from the iodide group by treatment with excess silver trifluoromethanesulfonate in a suitable solvent, e.g., acetonitrile, at reduced temperatures.

Once the desired activation has been carried out, introduction of the heteroarylium group can then proceed. One of the following three procedures has been found suitable for such introduction.

Method A:

The activated group is iodide and the addition of the heteroarylium group, e.g., pyridinium, is accomplished simply by treating with the corresponding heteroaryl, e.g., pyridine, in a suitable solvent, e.g., acetonitrile, at about room temperature.

Method B:

The activating group is trifluoromethanesulfonate and is formed in situ by treatment of the alcohol with trifluoromethanesulfonic acid anhydride in the presence of at least two equivalents of heteroaryl to provide the corresponding heteroarylium in a suitable solvent, e.g., dichloromethane, at reduced temperatures.

Method C:

The activated group is trifluoromethanesulfonate which is formed in situ by treatment of the iodide derivative with excess silver trifluoromethanesulfonate in a suitable solvent, e.g., acetonitrile, at reduced temperatures. As with Method A, the heteroaryl to provide the corresponding heteroarylium is simply added and displacement of the activating group then takes place directly.

Where the heteroarylium group has a substituent $R^c$, the most facile method of providing such a substituent is to employ as the reactant in the preparation methods described above a heteroaryl compound which already has the desired substituent. Such substituted heteroaryl compounds are readily available starting materials or may be prepared in a straight-forward manner using known literature methods.

In the preparation methods described above, the carboxyl group at the 3-position remains blocked by a carboxyl covering group until the final product is prepared. Then, if the anionic carboxylate is desired so as to form the zwitterionic internal salt, deblocking may be carried out in a conventional manner, with care being taken to avoid a procedure which is so harsh as to disrupt other portions of the final product molecule.

The general synthesis description above and the particular exemplifications which follow show the 6-(1-hydroxyethyl) moiety, which is preferred in most cases. However, it has been found that with certain 2-sidechain selections, the ultimate balance of favorable clinical properties in the overall molecule may be enhanced by selection of the 6-(1-fluoroethyl) moiety instead. Preparation of this and other 6-fluoroalkyl compounds within the scope of the present invention may be carried out in a straightforward manner using techniques well known in the art of preparing carbapenem antibacterial compounds. See, e.g., J. G. deVries et al., *Heterocycles*, 23 (8), 1915 (1985); J6-0163-882-A (Sanraku Ocean).

For all of the compounds exemplified herein, the R substituent is hydrogen, which is preferred. However, when R=methyl, the analogous 6-(1-hydroxyethyl) and 6-(1-fluoroethyl)carbapenems of the present invention are prepared in the manner described herein utilizing the appropriately chosen synthons which are known in the art. See, for example, L. M. Fuentes, I. Shinkai, and T. N. Salzmann, JACS, 108, 4675 (1986); and BE-900-718-A (Sandoz) respectively.

EXAMPLE 1

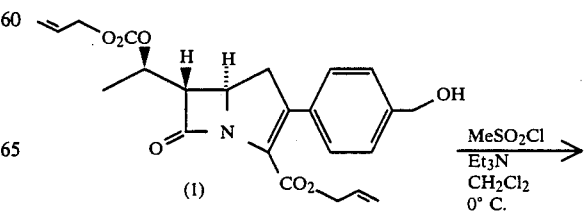

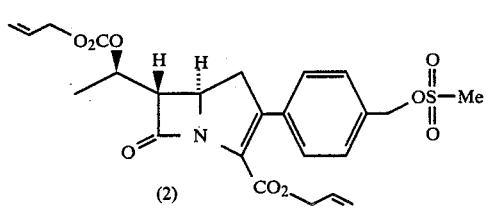

(2)

To a stirred solution of 42.7 mg (0.1 mmole) of 1 in 1 ml of sieve dried $CH_2Cl_2$ at 0° C. under a nitrogen atmosphere was added sequentially 15.2 mg (0.15 mmole) of neat $Et_3N$ and then 14.9 mg (0.13 mmole) of neat mesyl chloride. The resulting mixture was stirred for 15 minutes, and then partitioned between EtOAc, ice-$H_2O$, and some 2N HCl. The organic phase was separated, washed with saturated NaCl solution, dried over $Na_2SO_4$, filtered, evaporated, and dried in vacuo to give a quantitative yield of 2; IR ($CH_2Cl_2$): 1780, 1745, 1725 cm$^{-1}$; 200 MHz $^1$H-NMR (CDCl$_3$): δ1.49 (d, J=6.4 Hz, CH$_3$CH), 2.96 (s, CH$_3$SO$_3$), 3.18 (dd, J=9.9, 18.1 Hz, H-1), 3.34 (dd, J=8.9, 18.1 Hz, H-1), 3.43 (dd, J=2.8, 8.1 Hz, H-6), 4.30 (dt, J=2.3, 2.8 9.9 Hz, H-5), 4.66 (m, CH$_3$CHOH and CH$_2$CH=CH$_2$), 5.26 (m, OCH$_2$CH=CH$_2$), 5.29 (s, ArCH$_2$OSO$_2$), 7.40 (s, Ar-H). UV: $\lambda_{max}^{p\text{-}diox}=314$ nm.

EXAMPLE 2

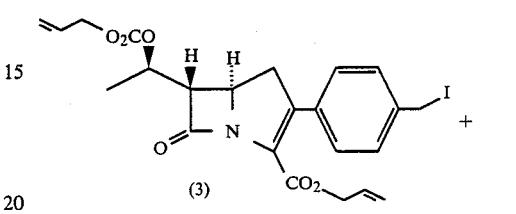

To a stirred solution of 38.8 mg (0.077 mmole) of 2 in 1 ml of acetone at 0° C. was added all at once 23 mg (0.15 mmole) of NaI. The ice-$H_2O$ bath was removed and the mixture stirred further under a nitrogen atmosphere for 0.5 hour. After this time, the resulting mixture was partitioned between EtOAc, ice-$H_2O$, 5% Na$_2$S$_2$O$_4$ (aq.) solution and saturated NaCl solution. The organic phase was separated, dried over Na$_2$SO$_4$, filtered, evaporated and dried in vacuo to give 3; IR (CH$_2$Cl$_2$): 1780, 1745, 1725 cm$^{-1}$; 200 MHz $^1$H-NMR (CDCl$_3$): δ1.49 (d, J=7.4 Hz, CH$_3$), 3.17 (dd, J=9.8, 18.1 Hz, H-1), 3.29 (dd, J=8.7, 18.1 Hz, H-1), 3.41 (dd, J=2.9, 8.7 Hz, H-6), 4.27 (dt, J=2.9, 8.7, 9.8 Hz, H-5), 4.65 (m, CH$_3$CHOH and OCH$_2$CH=CH$_2$), 5.26 (m, OCH$_2$CH=CH$_2$), 5.89 (m, OCH$_2$CH=CH$_2$), 7.32 (m, Ar-H). UV: $\lambda_{max}^{p\text{-}diox}=322$ nm.

METHOD A

EXAMPLE 3

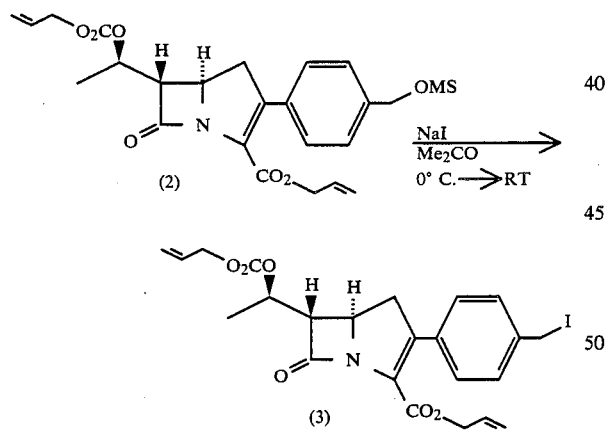

To a stirred solution of 161 mg (0.299 mmoles) of 3 in 5 ml of anhydrous acetonitrile was added 31.0 mg (0.33 mmoles) of solid 3-aminopyridine. The resulting solution was stirred at room temperature for 17.5 hours under a $N_2$ atmosphere and then partitioned between CH$_2$Cl$_2$ and ice/H$_2$O. The organic phase was separated, dried with anhydrous Na$_2$SO$_4$, filtered and concentrated under vacuum to provide 204.5 mg of residue as an orange film. The film was redissolved in 1 ml methylene chloride and the solution triturated with 12 ml Et$_2$O. The gummy solid which separated was collected and dried under vacuum to provide 189 mg (100%) of 4 as an orange foam; IR (CH$_2$Cl$_2$): 3280, 3160, 1785, 1745, 1725. cm$^{-1}$; 300 MHz $^1$H-NMR (CDCl$_3$): δ 1.47 (d, J=5.8 Hz, CH$_3$CH), 3.17 (dd, J=9.8, 19 Hz, H-1), 3.37 (dd, J=8.8, 19 Hz, H-1), 3.57 (dd, J=2.8, 7.4 Hz, H-6), 4.30 (dt, J=2.0, 9.8 Hz, H-5), 4.63 (d, J=6.2, OCH$_2$CH=CH$_2$), 4.65 (m, H-8), 5.25 (m, OCH$_2$CH=CH$_2$), 5.61 (s, ArCH$_2$), 5.88 (m, CH$_2$CH=CH$_2$), 6.29 (s, NH$_2$), 7.41 (d, J=8.3 Hz, Ar-H), 7.42 (t, pyridine-H-5), 7.49 (d, J=8.3 Hz, Ar-H), 7.63 (dd, J=1.5, 8.8 Hz, pyridine-H-3), 7.61 (d, J=5.5 Hz, pyridine-H-6), 8.98 (s, pyridine-H-2); UV: $\lambda_{max}^{p\text{-}diox}=307, 268$ (s) nm.

EXAMPLE 4

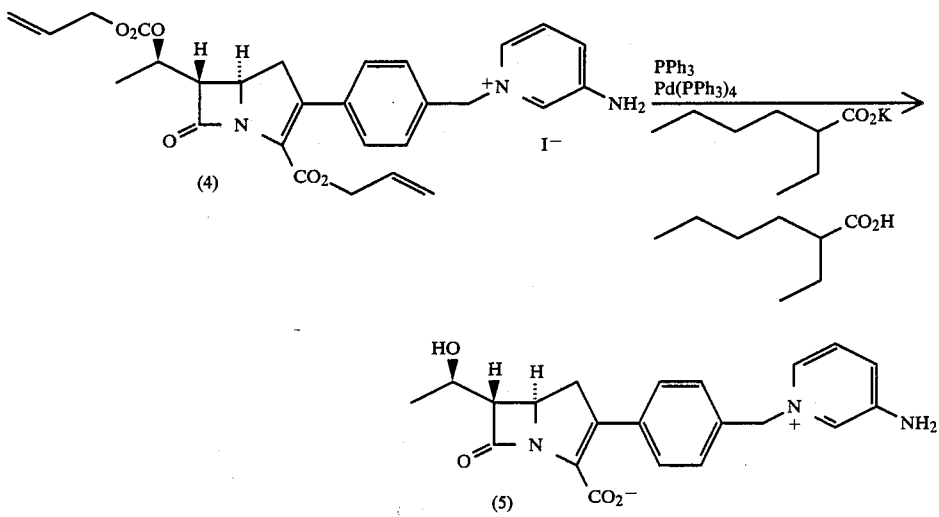

To a stirred solution of 157 mg (0.249 mmoles) of 4 in 5 ml anhydrous CH$_2$Cl$_2$ and 1.5 ml anhydrous EtOAc was added a mixture of 39.2 mg (0.149 mmoles) triphenylphosphine and 57.5 mg (0.0498 mmoles) of tetrakis (triphenylphosphine) palladium, followed by 43.7 µl (0.274 mmoles) of 2-ethyl hexanoic acid and 548 µl (0.274 mmoles) of 0.5M potassium 2-ethyl hexanoate in EtOAc. The mixture was stirred at room temperature for 5 hours under an N$_2$ atmosphere. A light colored precipitate developed after 10 minutes. The reaction slurry was then diluted with EtOAc and the solid separated and washed 3 times with Et$_2$O. The solid was then dried in vacuo and purified by reverse phase-PLC (3×1000 µ, 20×20 cm, reverse phase silica gel F plates, eluted at ~5° with 30% THF in H$_2$O). The major UV active product bands were combined and extracted 8 times with CH$_3$CN-H$_2$O (4:1). The combined aqueous extracts were washed 3 times with hexanes, filtered through a Gelman Acrodisc-CR 0.45 µ filter assembly and concentrated under vacuum. The concentrate was lyophilized to give 50.3 mg of 5 as an off white fluffy solid; IR (nujol mull): 3300, 3150, 1750, 1580 cm$^{-1}$; 200 MHz $^1$H-NMR (D$_2$O): δ 1.31 (d, J=6.3 Hz, CH$_3$CH), 3.13 (dd, J=9.8, 16.8 Hz, H-1), 3.41 (dd, J=8.57, 16.8 Hz, H-1), 3.50 (dd, J=2.3, 5.4 Hz, H-6), 4.38 (m, H-8 and H-5), 5.58 (s, PhCH$_2$), 7.39 (m, Ar-H and pyridine-H-5), 7.67 (m, pyridine-H-4), 8.10 (m, pyridine-H-2 and H-6); UV: $\lambda_{max}^{H2O}$=306, 254 nm.

METHOD B

EXAMPLE 5

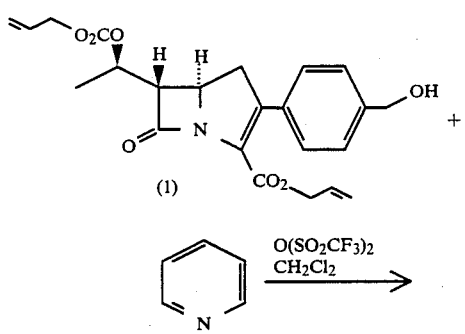

-continued

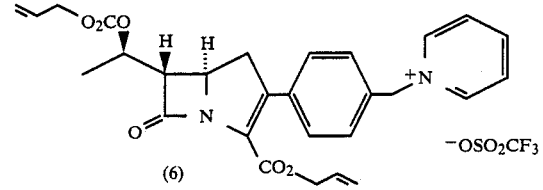

To a stirred solution of 117.4 mg (0.275 mmoles) of 1 in 5 ml anhydrous CH$_2$Cl$_2$ at −20° C. under a N$_2$ atmosphere was added 55.6 µl (0.687 mmoles) of pyridine, then 60.1 µl (0.357 mmoles) of trifluoromethanesulfonic anhydride. The resulting solution was stirred 2 hours at −20° C. and then partitioned between methylene chloride and ice/H$_2$O. The organic phase was separated, washed with saturated aqueous NaCl, dried with Na$_2$SO$_4$, filtered and concentrated under vacuum to provide 177.1 mg of a residue as a yellow film. The crude reaction residue was dissolved in methylene chloride and the solution triturated with ether. The gummy solid which separated was collected and dried under vacuum to provide 164.4 mg (94%) of 6, as a yellow foam; IR (CH$_2$Cl$_2$): 1785, 1745, 1725 cm$^{-1}$; 200 MHz NMR (CDCl$_3$): δ 147 (d, J=6.4 Hz, CH$_3$CH), 3.14 (dd, J=10.3, 18.5 Hz, H-1), 3.31 (dd, J=9.0, 18.5 Hz, H-1), 3.46 (dd, J=2.9, 7.9 Hz, H-6), 4.32 (dt, J=2.9, 9.8 Hz, H-5), 4.65 (m, H-8 and CH$_2$CH=CH$_2$), 5.25 (m, CH$_2$CH=CH$_2$), 5.87 (s, Ar-CH$_2$), 5.87 (m, CH$_2$CH=CH$_2$), 7.40 (d, J=8.2 Hz, Ar-H), 7.51 (d, J=8.2 Hz, Ar-H), 7.97 (t, J=6.7 Hz, pyridine-H-3 and H-5), 8.42 (t, J=6.5 Hz, pyridine-H-4), 9.06 (d, J=5.3 Hz, pyridine-H-2 and H-6); UV: $\lambda_{max}^{p\text{-}diox}$=316,266 nm.

METHOD C

EXAMPLE 6

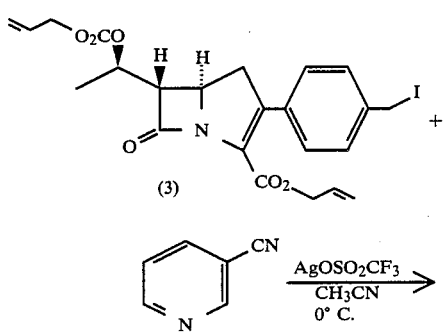

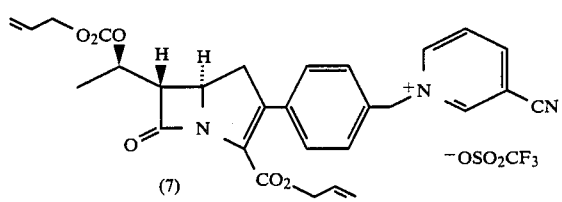

To a stirred solution of 58.8 mg (0.109 mmoles) of 3 in 1.5 ml anhydrous acetonitrile at 0° C. under a N₂ atmosphere was added a solution of 14.8 mg (0.142 mmoles) of nicotinonitrile in 200 μl anhydrous acetonitrile, followed by a solution of 64 mg (0.25 mmoles) of silver trifluoromethanesulfonate in 350 μl anhydrous acetonitrile. The resulting yellow slurry was stirred 1.5 hours at 0° C. then concentrated under vacuum. The residue was dissolved in CH₂Cl₂ and the mixture filtered through a Gelman Acrodisc-CR 0.45 μ filter assembly. The yellow filtrate was evaporated under vacuum to provide 72.4 mg of a residue, as a yellow film. The crude residue was dissolved in 1 ml methylene chloride and the solution triturated with 11 ml Et₂O. The solid which separated was collected and redissolved in CH₂Cl₂. The ether trituration was repeated twice and then the collected solid dried under vacuum to provide 45.1 mg (62%) of 7: IR (CH₂Cl₂): 1770, 1740, 1725 cm⁻¹; 200 MHz NMR (CDCl₃): δ 1.48 (d, J-6.1 Hz, CH₃CH), 3.14 (dd, J=10.2, 18.4 Hz, H-1), 3.35 (dd, J=8.5, 18.4 Hz, H-1), 3.49 (dd, J=2.5, 7.6 Hz, H-6), 4.28 (m, H-5), 4.65 (m, H-8 and CH₂CH=CH₂), 5.28 (m, CH₂CH=CH₂), 5.9 (m, CH₂CH=CH₂), 6.05 (s, Ar—CH₂), 7.42 (d, J=8.2 Hz, Ar-H and pyridine H-4), 7.56 (d, J=8.2 Hz, Ar-H), 8.33 (t, J=7.0 Hz, pyridine-H-5), 8.73 (d, J=7.6 Hz, pyridine-H-6), 9.32 (s, pyridine-H-2).

EXAMPLE 7

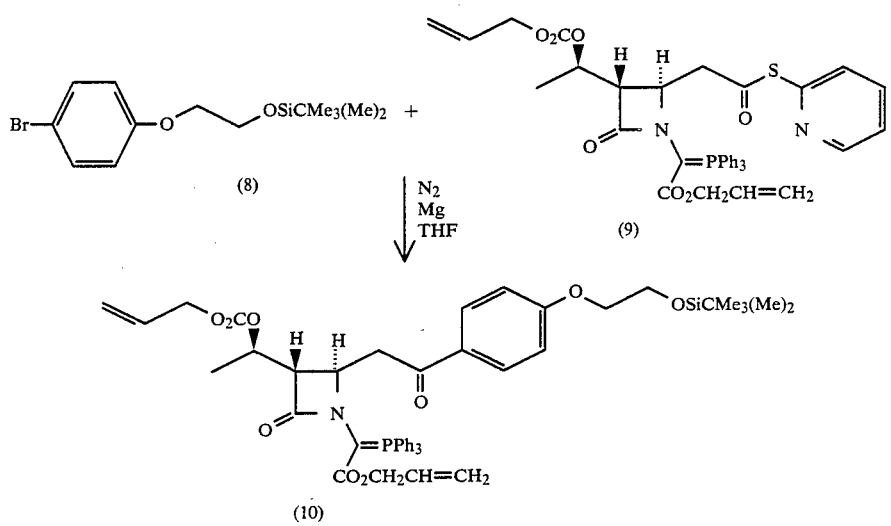

A mixture of magnesium (Mg) (38.9 mg, 1.6×10⁻⁴ moles) and aryl bromide (8) (234 mg, 7.1×10⁻⁴ moles) in 10 μl of 1,2-dibromoethane was stirred in 2 ml of freshly distilled tetrahydrofuran (THF) on a magnetic stirrer for 2 hrs. The reaction mixture was then drawn into a dry syringe and added to a solution of pyridyl thioester-ylid (9) (335.6 mg, 0.47 mmole) in 2 ml of distilled (THF) at 0 degrees C. under nitrogen, and the resulting intensely yellow solution was stirred for 0.5 hr. The reaction mixture was partitioned between ethyl acetate (EtOAc) / ice water / 1M ammonium chloride (NH₄Cl); and the organic phase was separated, washed sequentially with saturated sodium chloride (NaCl) solution, cold dilute aqueous sodium hydroxide (NaOH) solution, and saturated NaCl solution, dried over sodium sulfate (Na₂SO₄), filtered and evaporated. The product was then purified by plate layer chromatography, using 2×2000μ plates, eluting with diethyl ether (Et₂O), to give 250.6 mg of foamy product (10), a 62.7% yeild.

EXAMPLE 8

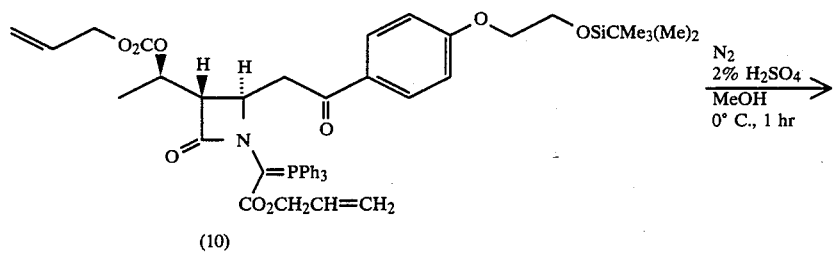

(10)

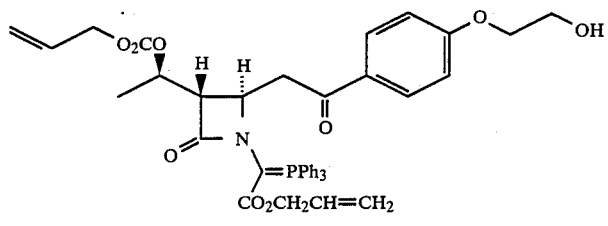

(11)

To a stirred solution of ketone-ylid derivative (10) (245.7 mg, 0.289 mmole) in 2 ml of methanol (CH$_3$OH) at 0 degrees C. under nitrogen was added 40 μl of concentrated sulfuric acid (H$_2$SO$_4$); and the reaction mixture was stirred under those conditions for 45 mins, after which it was partitioned between EtOAc / ice water / saturated sodium bicarbonate (NaHCO$_3$) solution. The organic phase was separated, washed with saturated NaCL solution, dried over Na$_2$SO$_4$, filtered and evaporated. The product was then purified by plate layer chromatography using 2000μ plates, eluting with EtOAc/Et$_2$O (2:1) to give 172.7 mg of desired product (11), and 81.2% yield.

EXAMPLE 9

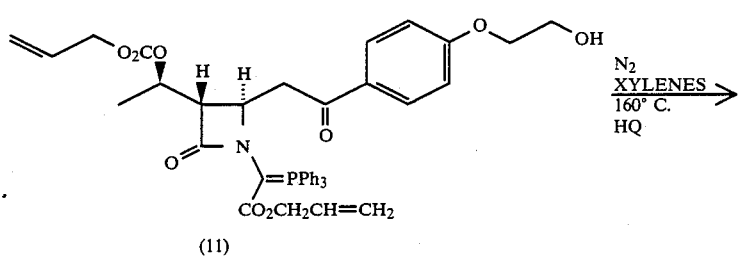

(11)

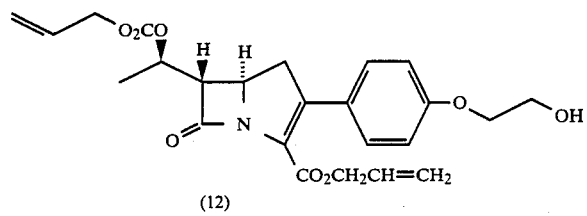

(12)

The phosphorane derivative (11) (170 mg, 2.31×10$^{-4}$ moles) in 10 ml of xylenes, mixed with a small amount of hydroquinone, was refluxed under nitrogen for 1.5 hours and allowed to cool. It was then evaporated under high vacuum and dried in vacuo. The product was purified by plate layer chromatography using a 2000μ plate, eluting with CH$_2$Cl$_2$/EtOAc (2:1), to give 65 mg of oily product (12), a 61.4% yield.

EXAMPLE 10

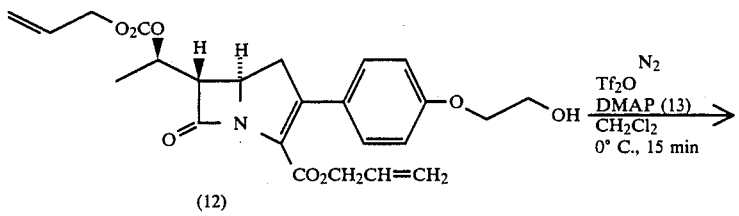

(12)

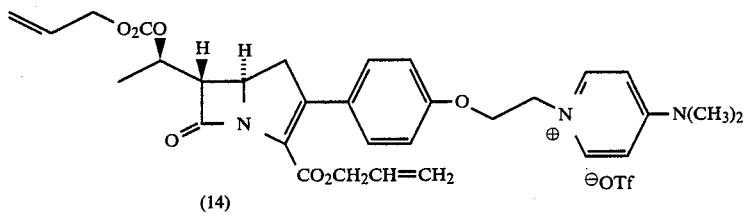

(14)

To a stirred mixture of carbapenem alcohol derivative (12) (47.7 mg, 1.03×10⁻⁴ moles) and dimethylaminopyridine (13) (27.6 mg, 2.26×10⁻⁴ moles) in 1 ml of sieve dried CH$_2$Cl$_2$ at 0 degrees C. under nitrogen was added neat trifluoromethanesulfonic acid anhydride (31.9 mg, 1.13×10⁻⁴ moles). The reaction mixture was stirred at 0 degrees C. under nitrogen for 15 mins, after which it was partitioned between CH$_2$Cl$_2$ and ice water. The organic phase was seperated, dried over Na$_2$SO$_4$, filtered, evaporated, and dried in vacuo to give 68.5 mg of desired final product (14), a 93.7% yield.

EXAMPLE 11

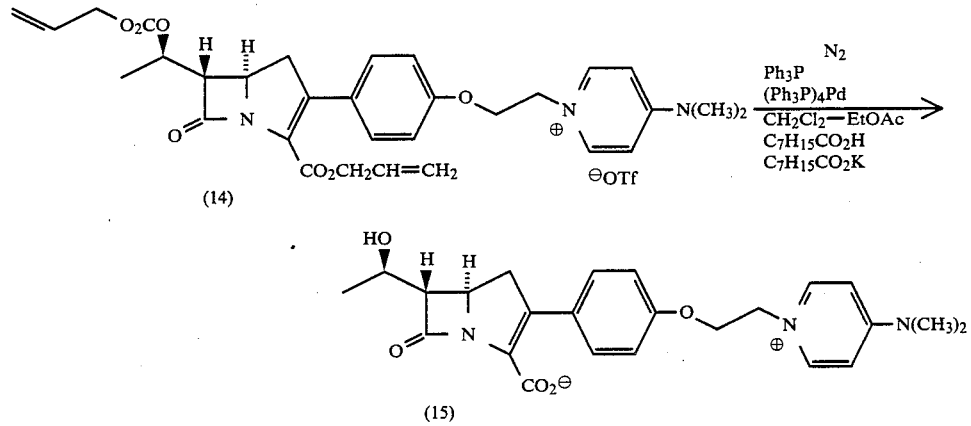

The penultimate product prior to deblocking (14) (66 mg, 9.28×10⁻⁵ moles) together with 2-ethyl hexanoic acid (14.7 mg, 1.02×10⁻⁴ moles), 0.5M potassium 2-ethyl hexanoate in EtOAc (204 μl, 1.02×10⁻⁴ moles), triphenylphosphine (14.6 mg, 5.6×10⁻⁵ moles), and tetrakistriphenylphosphinepalladium (21.4 mg, 1.86×10⁻⁵ moles) in 1.75 ml of CH$_2$Cl$_2$ and 0.25 ml of EtOAc at room temperature was stirred under nitrogen for 2.5 hrs. After this time the semi-solution was extracted with 6.7 ml of water under cold conditions with centrifugation. This procedure was repeated and the combined extracts were concentrated and then purified by reverse phase chromatography using 1×500μ plates, eluting with 30% tetrahydrofuran in water under cold conditions to give, after workup and lyophilization, 17.3 mg of final product (15) (42.6% yield).

EXAMPLES 12-49

Employing the procedures described above, additional compounds of the present invention were prepared. These are described in the table below, which additionally includes characterizing data and the method of preparation for each compound.

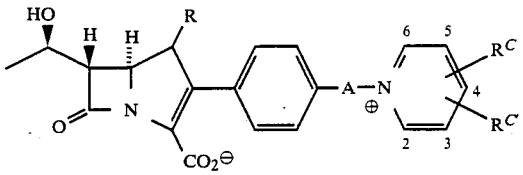

TABLE I

| Example No. | R | A | R$^c$ | R$^{c'}$ | $\lambda_{max}^{H2O}$ (nm) | Method of Preparation |
|---|---|---|---|---|---|---|
| 12 | H | —CH$_2$— | H | H | 257,303 | A or B |
| 13 | H | —CH$_2$— | 2-NH$_2$ | H | 303 | A |
| 14 | H | —CH$_2$— | 3-NH$_2$ | H | 308 | A |
| 15 | H | —CH$_2$— | 4-NH$_2$ | H | 274,301 | A |
| 16 | H | —CH$_2$— | 2-NHCH$_3$ | H | 307 | A |
| 17 | H | —CH$_2$— | 2-N(CH$_3$)$_2$ | H | 306 | B |
| 18 | H | —CH$_2$— | 4-N(CH$_3$)$_2$ | H | 300 | A or B |
| 19 | H | —CH$_2$— | 3-NHCH$_2$CO$_2$K | H | 267,306 | A |
| 20 | H | —CH$_2$— | 4-NHCH$_2$CO$_2$K | H | 287 | A |
| 21 | H | —CH$_2$— | 3-CO$_2$K | H | 305 | B |
| 22 | H | —CH$_2$— | 3-CON(CH$_3$)$_2$ | H | 304 | B |
| 23 | H | —CH$_2$— | 3-CN | H | 305 | C |
| 24 | H | —CH$_2$— | 3-CF$_3$ | H | 304 | C |
| 25 | H | —CH$_2$— | 3-SCH$_3$ | H | 228,274,306 | A |

TABLE I-continued

| Example No. | R | A | $R^c$ | $R^{c'}$ | $\lambda_{max}^{H2O}$ (nm) | Method of Preparation |
|---|---|---|---|---|---|---|
| 26 | H | —CH$_2$— | 4-φ | H | 300 | B |
| 27 | H | —CH$_2$— | 2-CH$_3$ | H | 267,304 | A or B |
| 28 | H | —CH$_2$— | 3-CH$_3$ | H | 304 | A or B |
| 29 | H | —CH$_2$— | 4-CH$_3$ | H | 304 | A or B |
| 30 | H | —CH$_2$— | 2-CH$_2$CH$_3$ | H | 268,304 | B |
| 31 | H | —CH$_2$— | 4-CH$_2$NH$_2$ | H | 304 | A |
| 32 | H | —CH$_2$— | 4-CH$_2$SO$_3$K | H | 304 | A |
| 33 | H | —CH$_2$— | 4-CH$_2$CH$_2$SO$_3$K | H | 304 | A |
| 34 | H | —CH$_2$— | 3-CH$_2$SCH$_3$ | H | 304 | A |
| 35 | H | —CH$_2$— | 3-CH$_2$SCH$_2$CH$_2$CN | H | 303 | A |
| 36 | H | —CH$_2$— | 3-CH$_2$SCH$_2$CF$_3$ | H | 303 | A |
| 37 | H | —CH$_2$— | 4-OH* | 3-CO$_2$K | 300,259 | A** |
| 38 | H | —CH$_2$— | 4-OH* | H | 302,265 | C*** |
| 39 | H | —CH$_2$— | 4-OMe | 3-CO$_2$Me | 304 | A |
| 40 | H | —CH$_2$— | 4-CH$_2$SMe | 3-NH$_2$ | 308 | A |
| 41 | H | —CH$_2$— | 3-NH$_2$ | 5-CH$_2$SMe | 309,260 | A |
| 42 | β-Me | —CH$_2$— | 4-NH$_2$ | H | 302,273 | A |
| 43 | H | —(CH$_2$)$_2$— | 3-NH$_2$ | H | 310 | C |
| 44 | H | —(CH$_2$)$_3$— | 3-NH$_2$ | H | 305 | C |
| 45 | H | —(CH$_2$)$_3$— | 4-NH$_2$ | H | 300,270 | A |
| 46 | H | —(CH$_2$)$_3$— | 3-CH$_2$SMe | H | 301,272 | C |
| 47 | α-Me | —CH$_2$— | 4-NH$_2$ | H | 302,273 | A |
| 48 | H | —CH$_2$— | 3-CH$_2$SMe | 4-NH$_2$ | 300,278 | A |
| 49 | H | —OCH$_2$CH$_2$— | H | 4-NMe$_2$ | 290 | B |

*These compounds actually exist as their pyridone tautomers:

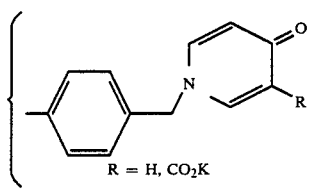

R = H, CO$_2$K

**Performed with N 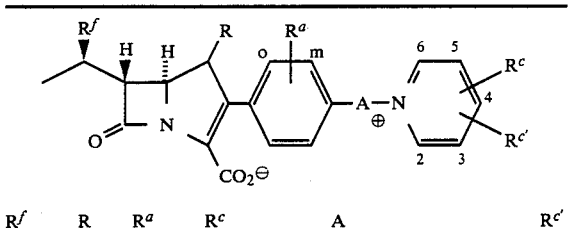

***Performed with N 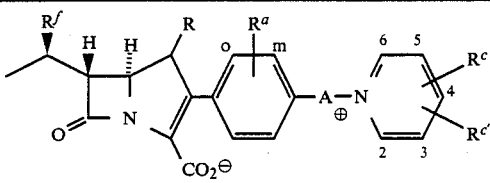

EXAMPLE 50

Following the procedures described above, additional compounds of the present invention may be prepared, as set forth in the following table.

TABLE II

| $R^f$ | R | $R^a$ | $R^c$ | A | $R^{c'}$ |
|---|---|---|---|---|---|
| —OH | H | H | 2-NH$_2$ | —CH$_2$CH$_2$— | H |
| —OH | H | H | 3-CH$_2$SCH$_3$ | —SCH$_2$CH$_2$— | H |
| —OH | H | H | 4-NH$_2$ | —CH$_2$SCH$_2$— | H |
| —F | H | H | 3-CH$_2$SCH$_3$ | —CH$_2$— | H |
| —F | CH$_3$ | H | 3-SCH$_3$ | —CH$_2$— | H |
| —OH | H | H | 3-F | —CH$_2$— | H |
| —OH | H | m-CH$_3$ | 2-NH$_2$ | —CH$_2$— | H |
| —OH | H | m-F | 3-CH$_2$SCH$_3$ | —CH$_2$— | H |
| —OH | H | m-OH | 3-CH$_2$SCH$_3$ | —CH$_2$— | H |

TABLE II-continued

| $R^f$ | R | $R^a$ | $R^c$ | A | $R^{c'}$ |
|---|---|---|---|---|---|
| —OH | CH$_3$ | H | 2-NH$_2$ | —CH$_2$— | H |
| —OH | H | H | 4-NH$_2$ | —CH$_2$— | 3-CH$_2$SMe |
| —OH | H | H | 3-CH$_2$CO$_2$K | —CH$_2$— | 5-CH$_2$COOK |

What is claimed is:
1. A compound of the formula:

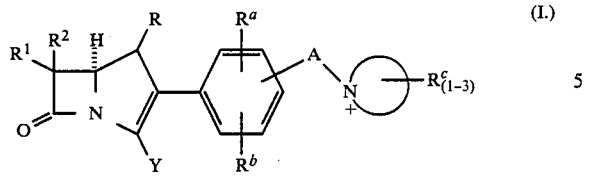

(I.)

wherein:

R is H or CH₃;

R¹ and R² are independently H, CH₃—, CH₃CH₂—, (CH₃)₂CH—, HOCH₂—, CH₃CH(OH)—, (CH₃)₂C(OH—, FCH₂CH(OH)—, F₂CHCH(OH)—, F₃CCH(OH)—, CH₃CH(F)—, CH₃CF₂—, or (CH₃)₂C(F)—;

Rᵃ, Rᵇ and Rᶜ (Rᶜ represents from 1 to 3 substituents which may be the same or different and is (are) on the carbon ring atom(s) or nitrogen heteroatom(s), if such is (are) present) are independently selected from the group consisting of:

(a) a trifluoromethyl group: —CF₃;
(b) a halogen atom: —Br, —Cl, —F, or —I;
(c) C₁–C₄ alkoxy radical: —OC₁₋₄ alkyl;
(d) a hydroxy group: —OH;
(e) (C₁–C₆ alkyl) carbonyloxy radical:

alkyl;

(f) a carbamoyloxy radical which is unsubstituted or substituted on nitrogen with one or two C₁–C₄ alkyl groups:

where Rʸ and Rᶻ are independently H or C₁₋₄ alkyl;

(g) a C₁–C₆ alkylthio radical, C₁–C₆ alkylsulfinyl radical or C₁–C₆ alkylsulfonyl radical:

alkyl where n=0–2, and the alkyl portion is optionally substituted by cyano;

(h) a sulfamoyl group which is unsubstituted or substituted on nitrogen by one or two C₁–C₄ alkyl groups:

where Rʸ and Rᶻ are as defined above;

(i) an amino group, or a mono (C₁–C₄ alkyl) amino or di(C₁–C₄ alkyl)amino group:

where Rʸ and Rᶻ are as defined above;

(j) a formylamino group:

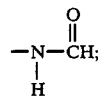

(k) (C₁–C₆ alkyl)carbonylamino radical:

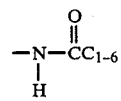

alkyl;
alkyl;

(l) a (C₁–C₄ alkoxy) carbonylamino radical:

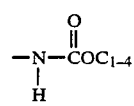

alkyl;

(m) a ureido group in which the terminal nitrogen is unsubstituted or substituted with one or two C₁–C₄ alkyl groups:

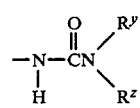

where Rʸ and Rᶻ are as defined above;

(n) a sulfonamido group:

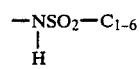

alkyl;

(o) a cyano group: —CN;
(p) a formyl or acetalized formyl radical:

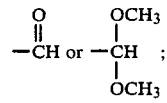

(q) (C₁–C₆ alkyl) carbonyl radical wherein the carbonyl is free or acetalized:

alkyl or

alkyl;
(r) phenylcarbonyl:
(s) a hydroximinomethyl radical in which the oxygen or carbon atom is optionally substituted by a $C_1$–$C_4$ alkyl group:

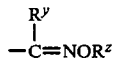

where $R^y$ and $R^z$ are as defined above;
(t) a ($C_1$–$C_6$ alkoxy)carbonyl radical:

alkyl;
(u) a carbamoyl radical which is unsubstituted or substituted on nitrogen by one or two $C_1$–$C_4$ alkyl groups:

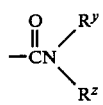

where $R^y$ and $R^z$ are as defined above;
(v) an N-hydroxycarbamoyl or N($C_1$–$C_4$ alkoxy)-carbamoyl radical in which the nitrogen atom may be additionally substituted by a $C_1$–$C_4$ alkyl group:

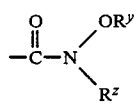

where $R^y$ and $R^z$ are as defined above;
(w) a thiocarbamoyl group:

(x) an amidino group

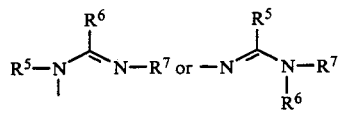

where $R^5$, $R^6$ and $R^7$ are independently hydrogen, $C_1$–$C_4$alkyl or wherein two of the alkyl groups together form a $C_2$–$C_6$alkylidene radical optionally interrupted by a heteroatom and joined together to form a ring;
(y) a carboxamidino group

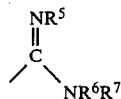

where $R^5$, $R^6$ and $R^7$ are as defined above;
(z) a guanidinyl group where $R^6$ in (y) above is $NR^8R^9$ and $R^8$ and $R^9$ are as defined for $R^5$ through $R^7$ above;
(aa) hydrogen;
(ab) $C_2$–$C_6$ alkenyl radical;
(ac) $C_2$–$C_6$ alkynyl radical;
(ad) $C_3$–$C_7$ cycloalkyl radical;
(ae) $C_3$–$C_7$ cycloalkyl methyl radical;
(af) $C_5$–$C_7$ cycloalkenyl radical;
(ag) phenyl, except that only $R^c$ may be phenyl;
(ah) $C_1$–$C_6$ alkyl radical;
(ai) $C_1$–$C_4$ alkyl monosubstituted by one of the substituents (a)–(ag) above;
(aj) an anionic function selected from the group consisting of: phosphono [P=O(OM$^c$)$_2$]; alkylphosphono {P=O(OM$^c$)—[O($C_1$–$C_4$ alkyl)]}; alkylphosphinyl [P=O(OM$^c$)—($C_1$–$C_4$alkyl)]; phosphoramido [P=O(OMc)N(R$^y$)R$^z$ and P=O(OM$^c$)NHR$^x$]; sulfino (SO$_2$M$^c$); sulfo (SO$_3$M$^c$); acylsulfonamides selected from the structures CONM$^c$SO$_2$R$^x$, CONM$^c$SO$_2$N(R$^y$)R$^z$, SO$_2$NM$^c$CON(R$^y$)R$^z$; and SO$_2$NM$^c$CN, where $R^x$ is phenyl or heteroaryl, where heteroaryl is as defined below except that there is no quaternary nitrogen and attachment through nitrogen is optional; and the phenyl and heteroaryl are optionally mono-substituted by $R^q$; M$^c$ is hydrogen or an alkali metal; $R^y$ and $R^z$ are as defined above; where $R^q$ is a member selected from the group consisting of —OH; —OCH$_3$—; —CN; —C(O)NH$_2$; —OC(O)NH$_2$; —OC(O)N(CH$_3$)$_2$; —SO$_2$NH$_2$; —SO$_2$N(CH$_3$)$_2$; —SOCH$_3$; —F; —CF$_3$; tetrazolyl; and —COOM$^a$, where M$^a$ is hydrogen, alkali metal, methyl or phenyl;

A is para (p) or meta (m) with respect to the point of attachment of the phenyl ring to the carbapenem nucleus, and is (CH$_2$)$_m$—Q—(CH$_2$)$_n$, where m is 0 to 2 and n is 1 or 2; and Q is a covalent bond; O; S; SO; SO$_2$; NH; or N($C_1$–$C_4$ alkyl);

is a monocyclic aromatic hydrocarbon group having 5 or 6 ring atoms in which one of the carbon atoms has been replaced by a nitrogen atom and attachment of said group is by way of said nitrogen atom; and said nitrogen atom is, furthermore, quaternary by virtue of the attachment bond and the ring bonds; and in which one additional carbon atom is optionally replaced by a heteroatom selected from O and S, or from 1 to 3 additional carbon atoms are each optionally replaced by a nitrogen heteroatom selected from O and S, or from 1 to 3 additional carbon atoms are each optionally replaced by a nitrogen heteroatom; and Y is selected from:
(i) COOH or a pharmaceutically acceptable ester thereof;

(ii) COOM wherein M is an alkali metal or other pharmaceutically acceptable salt;
(iii) COOM wherein M is a negative charge in the case where a permanent positive charge exists elsewhere in the molecule.

2. A compound according to claim 1 wherein $R^1/R^2$ is H— and $R^2/R^1$ is $CH_3CH(OH)$—.

3. A compound according to claim 1 wherein $R^1/R^2$ is H— and $R^2/R^1$ is $CH_3CH(OH)$—; and A is —$CH_2$—.

4. A compound according to claim 1 wherein $R^1/R^2$ is H— and $R^2/R^1$ is $CH_3CH(OH)$—; and A is —$CH_2$—;

is selected from the group consisting of:

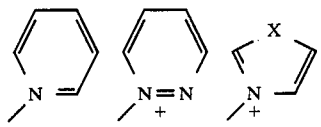

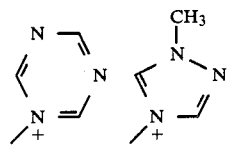

where X=O, S, or $NR^e$, where $R^e=C_1-C_4$alkyl, or $CH_2COR^f$, where $R^f=OCH_3$, $OCH_2$—(phenyl), $NH_2$, $CH_2SO_3^-M^+$, or $O^-M^+$, where $M^+=Na^+$ or $K^+$.

5. A compound according to claim 1 wherein $R^1/R^2$ is H— and $R^2/R^1$ is $CH_3CH(OH)$—; A is —$CH_2$—; and $-^+N\bigcirc$ is [pyridinium structure].

6. A compound according to claim 1 wherein the compound is selected from the group consisting of

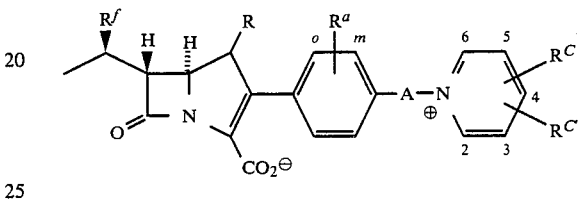

| $R^f$ | R | $R^a$ | A | $R^c$ | $R^{c'}$ |
|---|---|---|---|---|---|
| OH | H | H | —$CH_2$— | H | H |
| OH | H | H | —$CH_2$— | 2-$NH_2$ | H |
| OH | H | H | —$CH_2$— | 3-$NH_2$ | H |
| OH | H | H | —$CH_2$— | 4-$NH_2$ | H |
| OH | H | H | —$CH_2$— | 2-$NHCH_3$ | H |
| OH | H | H | —$CH_2$— | 2-$N(CH_3)_2$ | H |
| OH | H | H | —$CH_2$— | 4-$N(CH_3)_2$ | H |
| OH | H | H | —$CH_2$— | 3-$NHCH_2CO_2K$ | H |
| OH | H | H | —$CH_2$— | 4-$NHCH_2CO_2K$ | H |
| OH | H | H | —$CH_2$— | 3-$CO_2K$ | H |
| OH | H | H | —$CH_2$— | 3-$CON(CH_3)_2$ | H |
| OH | H | H | —$CH_2$— | 3-CN | H |
| OH | H | H | —$CH_2$— | 3-$CF_3$ | H |
| OH | H | H | —$CH_2$— | 3-$SCH_3$ | H |
| OH | H | H | —$CH_2$— | 4-$\phi$ | H |
| OH | H | H | —$CH_2$— | 2-$CH_3$ | H |
| OH | H | H | —$CH_2$— | 3-$CH_3$ | H |
| OH | H | H | —$CH_2$— | 4-$CH_3$ | H |
| OH | H | H | —$CH_2$— | 2-$CH_2CH_3$ | H |
| OH | H | H | —$CH_2$— | 4-$CH_2NH_2$ | H |
| OH | H | H | —$CH_2$— | 4-$CH_2SO_3K$ | H |
| OH | H | H | —$CH_2$— | 4-$CH_2CH_2SO_3K$ | H |
| OH | H | H | —$CH_2$— | 3-$CH_2SCH_3$ | H |
| OH | H | H | —$CH_2$— | 3-$CH_2SCH_2CH_2CN$ | H |
| OH | H | H | —$CH_2$— | 3-$CH_2SCH_2CF_3$ | H |
| OH | H | H | —$CH_2$— | 4-OH | 3-$CO_2K$ |
| OH | H | H | —$CH_2$— | 4-OH | H |
| OH | H | H | —$CH_2$— | 4-OMe | 3-$CO_2Me$ |
| OH | H | H | —$CH_2$— | 4-$CH_2SMe$ | 3-$NH_2$ |
| OH | H | H | —$CH_2$— | 3-$NH_2$ | 5-$CH_2SMe$ |
| OH | $\beta$-Me | H | —$CH_2$— | 4-$NH_2$ | H |
| OH | H | H | —$(CH_2)_2$— | 3-$NH_2$ | H |
| OH | H | H | —$(CH_2)_3$— | 3-$NH_2$ | H |
| OH | H | H | —$(CH_2)_3$— | 4-$NH_2$ | H |
| OH | H | H | —$(CH_2)_3$— | 3-$CH_2SMe$ | H |
| OH | $\alpha$-Me | H | —$CH_2$— | 4-$NH_2$ | H |
| OH | H | H | —$CH_2$— | 3-$CH_2SMe$ | 4-$NH_2$ |
| OH | H | H | —$OCH_2CH_2$— | H | 4-$NMe_2$ |
| —OH | H | H | —$CH_2CH_2$— | 2-$NH_2$ | H |
| —OH | H | H | —$SCH_2CH_2$— | 3-$CH_2SCH_3$ | H |

-continued

| $R^f$ | R | $R^a$ | A | $R^c$ | $R^{c'}$ |
|---|---|---|---|---|---|
| —OH | H | H | —CH$_2$SCH$_2$— | 4-NH$_2$ | H |
| —F | H | H | —CH$_2$— | 3-CH$_2$SCH$_3$ | H |
| —F | CH$_3$ | H | —CH$_2$— | 3-SCH$_3$ | H |
| —OH | H | H | —CH$_2$— | 3-F | H |
| —OH | H | m-CH$_3$ | —CH$_2$— | 2-NH$_2$ | H |
| —OH | H | m-F | —CH$_2$— | 3-CH$_2$SCH$_3$ | H |
| —OH | H | m-OH | —CH$_2$— | 3-CH$_2$SCH$_3$ | H |
| —OH | CH$_3$ | H | —CH$_2$— | 2-NH$_2$ | H |
| —OH | H | H | —CH$_2$— | 4-NH$_2$ | 3-CH$_2$SMe |
| —OH | H | H | —CH$_2$— | 3-CH$_2$CO$_2$K | CH$_2$COOK |

7. A pharmaceutical composition for antibacterial use comprising an antibacterially effective amount of a compound of claim 1 and a pharmaceutically acceptable carrier thereof.

8. A method of treating bacterial infections in human or animal subjects in need of such treatment comprising administering to such subject an antibacterially effective amount of a compound of claim 1.

9. The combination of a compound of claim 1 and a DHP inhibitor.

10. The combination of a compound of claim 6 and the DHP inhibitor 7-(L-2-amino-2carboxyethylthio)-2-(2,2-dimethylcyclopropanecarboxamide)-2-heptenoic acid.

11. A pharmaceutical composition for antibacterial use comprising an antibacterially effective amount of a compound of claim 1, an inhibitorily effective amount of a DHP inhibitor, and, optionally, a pharmaceutically acceptable carrier thereof.

12. A pharmaceutical composition according to claim 11 wherein the DHP inhibitor is 7-(L-2-amino-2-carboxyethylthio)-2-(2,2-dimethylcyclopropanecarboxamide)-2-heptenoic acid.

13. A method of treating bacterial infections in human or animal subjects in need of such treatment comprising coadministering to such subject an antibacterially effective amount of a compound of claim 1 and an inhibitorily effective amount of a DHP inhibitor.

14. A method according to claim 13 wherein the DHP inhibitor is 7-(L-2-amino-2-carboxyethylthio)-2(2,2-dimethylcyclopropanecarboxamide)-2-heptenoic acid.

* * * * *